(12) United States Patent
Inglis et al.

(10) Patent No.: US 6,224,930 B1
(45) Date of Patent: *May 1, 2001

(54) METHOD AND APPARATUS FOR THE APPLICATION OF VOLATILE SUBSTANCES CONVEYED IN CARRIER GAS

(75) Inventors: Andrew S. Inglis, Wybong; David J. Lark, Woodburn, both of (AU)

(73) Assignee: Vaporex PTY Ltd., New South Wales (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/771,400

(22) Filed: Dec. 20, 1996

(30) Foreign Application Priority Data

Dec. 20, 1995 (AU) .................................... PN7240

(51) Int. Cl.$^7$ ........................................ A23L 3/00
(52) U.S. Cl. ................. 426/320; 426/335; 426/532
(58) Field of Search .................... 426/320, 262, 426/263, 270, 335, 532, 654

(56) References Cited

U.S. PATENT DOCUMENTS

| 1,703,782 | * | 2/1929 | Schmidt | 426/320 |
|---|---|---|---|---|
| 2,131,134 | * | 9/1938 | Baer et al. | 426/320 |
| 2,150,827 | * | 3/1939 | Ginaca | 426/320 |
| 2,665,217 | | 1/1954 | Meuli . | |
| 3,506,458 | * | 4/1970 | Martin | 426/320 |
| 4,834,997 | * | 5/1989 | Howard | 426/320 |
| 5,445,792 | | 8/1995 | Rickloff et al. | 422/28 |

FOREIGN PATENT DOCUMENTS

| 33362-89 | | 4/1989 | (AU) . | |
|---|---|---|---|---|
| 65769-90 | | 5/1990 | (AU) . | |
| 26 38 355 | | 8/1976 | (DE) . | |
| 2 002 247 | | 3/1988 | (ES) . | |
| 2520592 | | 8/1983 | (FR) . | |
| 245671 | * | 1/1926 | (GB) | 426/320 |
| 94 11035 | | 5/1994 | (WO) . | |

OTHER PUBLICATIONS

Lueck, E., Antimicrobial food additives. Characteristics, Uses, Effects. ISBN: 3–540–10056–3, 81(02):T0053, FSTA, 1980.*

Patent Abstracts of Japan, Publication No. 06099051 dated Apr. 12, 1994, application No. 04221213 dated Aug. 20, 1992.

* cited by examiner

Primary Examiner—Leslie Wong
(74) Attorney, Agent, or Firm—McDermott, Will & Emery

(57) ABSTRACT

The invention relates to a method and apparatus for treating a perishable material particularly foodstuffs, pharmaceuticals and the like to extend the shelf life thereof including placing a material to be treated in a vessel capable of evacuation, evacuating the vessel and contacting the material with a volatile substance entrained in a carrier gas, the substance being capable of physical and/or chemical alteration of said material. Preferably the volatile substance is an antimocrobial volatile substance, e.g. a natural food acid such as acetic or carbonic acid, and the carrier gas is nitrogen or carbon dioxide.

30 Claims, 3 Drawing Sheets

METHOD AND APPARATUS FOR THE APPLICATION OF VOLATILE SUBSTANCES CONVEYED IN CARRIER GAS

This invention relates to a method and apparatus for the treatment of a perishable material with a volatile substance via a carrier gas or gases.

BACKGROUND OF THE INVENTION

Hitherto, conventional gaseous processes aimed at extending the shelf life of perishable materials have relied on modified atmosphere packaging (MAP) procedures. In such procedures, the oxygen gas atmosphere surrounding the substance is replaced with a food grade carbon dioxide and/or nitrogen atmosphere, and high barrier colaminate packaging is used to maintain the exclusion of oxygen from the package. The slight acidity produced by the carbonic acid which results from the exposure of the substance to carbon dioxide produces a fungicidal effect.

MAP processes have disadvantages, however. While it has been found that such procedures do extend the shelf life in respect of treated substances, the extension is limited and considerable costs are involved including the cost of the specialized colaminate film packaging.

In accordance with the present invention, there is provided a method and apparatus to effectively treat a perishable material with volatile substances by use of a carrier gas or gases to physically or chemically alter the material to preserve it against fungal or bacterial spoilage or other hazards thereby extending its shelf-life.

SUMMARY OF THE INVENTION

According to a first aspect, the present invention provides a method of treating a perishable material to preserve it comprising the steps of: placing the material in a vessel capable of evacuation; evacuating the vessel; and contacting the material with a volatile substance capable of physically or chemically altering the material, the substance being entrained in a carrier gas. Optionally, method steps (b) and (c) are repeated in sequence, as necessary, to achieve the desired aim.

According to a second aspect the invention provides an apparatus for treating a material comprising: a vessel for receiving the material; means for evacuating the vessel; means for entraining a volatile substance in a carrier gas; and means for contacting the material contained in the vessel with the volatile substance entrained in the carrier gas.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

Figure 1:
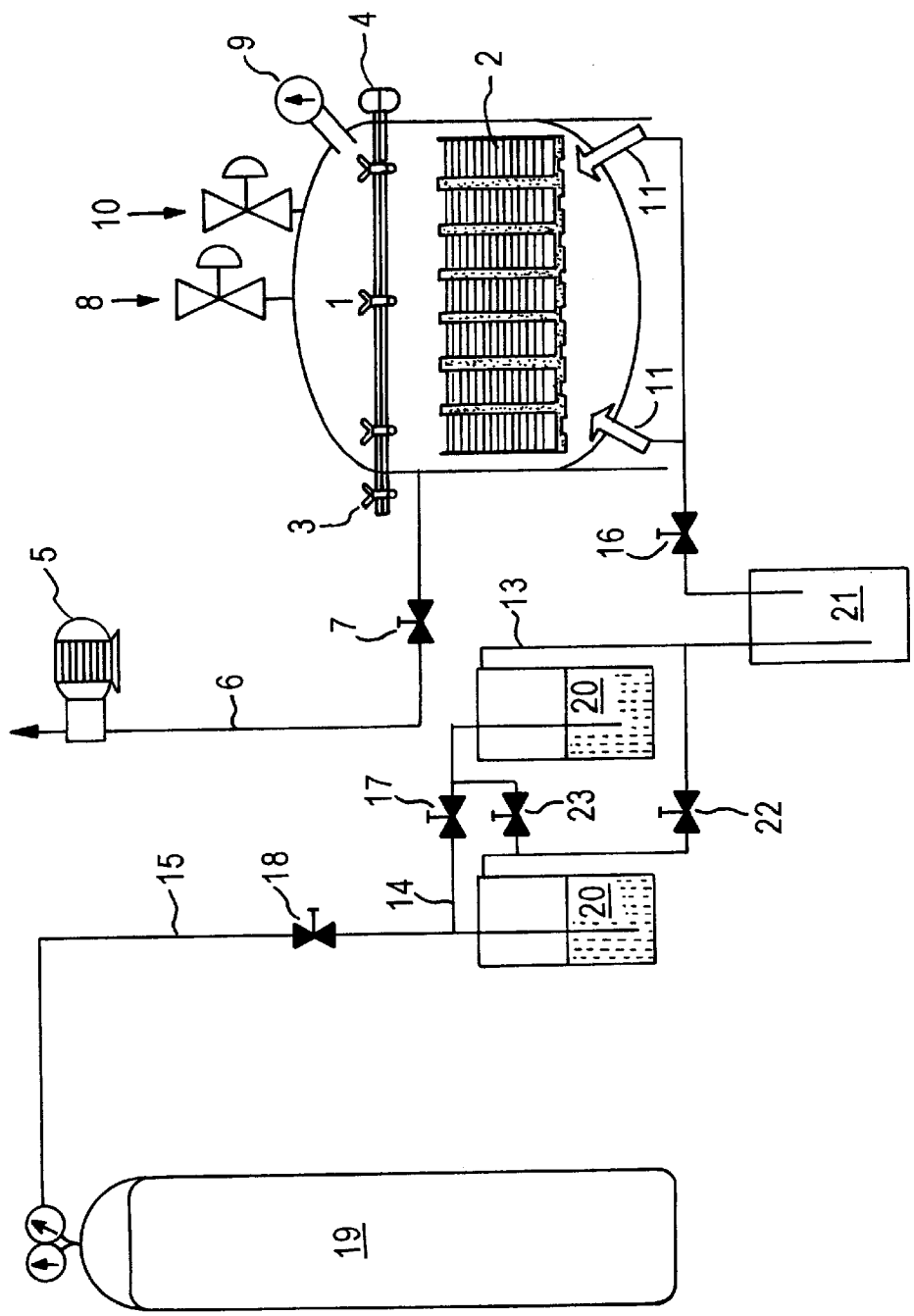
FIG. 1 is a schematic elevational representation of a batch treatment apparatus according to a first embodiment of the present invention.

Perishable materials that can be treated in accordance with the present invention include any material which is desired to have its chemical and/or physical characteristics altered by means of volatile substances to preserve it and thereby extend its shelf life. The method of the present invention is suitable for microbial decontamination and/or control of a wide range of food and other products including baked goods such as bread, whole grain cereals, whole or diced berries, fruits or vegetables, prepared salads, nuts in their shell, nut meats in storage awaiting drying or while undergoing further processing, vacuum packed smallgoods, cured meats, chicken flesh, carcass on abattoir chains, herbs and spices and the like.

The preservative effect of the method of the subject invention includes one or a combination of color, flavor and texture stabilization as well as resistance to or control of microbial infestation. It has been found that significant extensions in shelf life of baked goods and smallgoods (up to and exceeding 30 days) have been achieved by the preservative effect of the subject method. The method of the present invention is also suitable for microbial decontamination and/or control of pharmaceuticals and equipment including individual pharmaceutical ingredients.

While the inventive method may be used in isolation, it is also suitable for use with other treatment processes including, example, optimizing dosing with anti-oxidants where high surface concentrations are desired, for the delivery of soluble food grade or other preservatives, depositing of substances onto surfaces with the possible assistance of electrostatic charges or in conjunction with conventional MAP to increase the shelf life of certain products.

The volatile substance can be any such agent, particularly an antimicrobial agent, which may be conveyed by an inorganic or organic gas and which will chemically and/or physically alter the treated material to achieve the desired result. For example, for substantially extending the shelf life of foods particularly baked goods, the volatile substance is preferably a natural food acid, most preferably acetic acid and/or carbonic acid, although any other natural food acid having fungicidal or preserving qualities can be used. Alternatively, a potentially residual free chemical biocide, such as hydrogen peroxide, can be used. Mixtures of such volatile substances may also be used with the inventive method.

The volatile substance is preferably entrained in the carrier gas by passing the carrier gas through a vessel containing it. The carrier gas, which is substantially stripped of the volatile substance after contact with the material to be treated, may be recycled through the process. Alternatively, the volatile substance can be prepackaged with the carrier gas. The carrier gas is preferably carbon dioxide, nitrogen or mixtures thereof which can be sourced from a cylinder containing the relevant compressed gas(es). The carrier gas is preferably saturated with the volatile substance. Alternatively, at lower concentrations of the volatile substance, the method is less biocidal and more inhibitory.

The method of the invention can be performed either as a batch method or in a continuous flow mode. When a batch method is used, wrapped, unsealed material is preferably manually loaded and unloaded into the vessel. When a continuous flow mode is desired, commercially available flow wrapping equipment utilizing a conveyor and/or exposure in a suitable treatment tunnel can be used. The means for evacuating the vessel is preferably provided by an external vacuum source. The material to be treated is preferably first evacuated rapidly to sub-ambient pressure. The material contained in the evacuated vessel is preferably contacted with the carrier gas/volatile substance by means of one or more spargers.

For reducing the microbial content of a material, the duration of exposure is that required to sufficiently reduce the total viable microbial content to a desired value and is dependant on a number of variables including surface area of the material to be treated; degree of vacuum; overpressure; flow rates of the carrier gas; water activity ($A_w$); type and concentration of volatile substance and bacterial and fungal bioburden of the material. The efficiency of the treatment method is also dependant on the interaction between the matrix geography and/or chemistry and the added volatile substance.

Certain perishable materials must be treated individually if their matrix or final package configuration is such that, if treated simultaneously, they would present a physical barrier to the volatile substance contacting the surface interface of the materials to be treated. Several cycles of vacuum and exposure may be required depending on the goods being treated and the concentration of volatile substance entrained in the carrier gas. In the case of foods, the limit to which the material to be treated can be exposed to the carrier gas/volatile substance is generally determined by the flavor resultant from the acidulation of the product. As will be explained in more detail later, certain volatile antimicrobial substances, e.g. acetic acid, have an unfavorable effect on flavor due to acidulation. Other volatile substances, e.g. carbonic acid, cause little organoleptically detectable acidulation and can in some cases actually impart a smoked flavor and/or aroma to some smallgoods.

Further, some low acid foods particularly smallgoods will, following treatment in accordance with the inventive method, achieve additional color stability, particularly where carbonic acid is utilized as the volatile substance. Manufacturers of bland smallgoods e.g. lower priced sandwich-type hams, and the like can overcome mild acidulation by making slight changes to their flavor formulations. In some cases, however, the additional acidulation actually aids in completion and enhancement of the flavor profile while achieving near to, or complete microbial stability.

The applicants have noted that the acidic flavor effects resulting from the present inventive method may recede during storage. In all materials tested to date, flavor effects have in fact receded dramatically during the initial 24 hours following exposure, then more gradually thereafter. Certain materials are heated or cooked after treatment in accordance with the present method which further decreases any lingering unfavorable flavor effects of the treatment. This effect is particularly noted in bland baked goods such as crumpets.

Packaging materials with poor gas barrier properties or small perforations may also assist in the diffusion of volatile substances from the surface of materials treated by the inventive method thus reducing any acidic flavors. Conversely, packaging materials with excellent gas barrier properties will maintain an atmosphere of the volatile substances thus enhancing their preservative effect. Accordingly, the barrier properties of the packaging may be chosen to suit the treated material with these objectives in mind.

While particularly suited to use with water soluble volatiles, the inventive method may also be used with other applications such as those requiring the transfer of volatile substances that are not soluble in water e.g. some antioxidants.

The material to be treated e.g. foodstuffs, should ideally have a minimum water activity ($A_w$) of approximately 0.85 to allow the volatile substance to quickly transfer across from the carrier gas. An $A_w$ of approximately 0.95 will allow near optimum transference rates and therefore minimum exposure times. To optimize transfer rates it may be appropriate to dose all the gaseous mixture required to an overpressure of 0.01–0.2 bar (7.5–150 mm Hg) and up to 3 bar (2250 mm Hg) over atmospheric pressure and allow the appropriate contact time. Lower $A_w$ foodstuffs may require longer exposure times without the addition of a small quantity of water, generally 1–2% by weight, based on the weight of the material to be treated, onto the surface. This additional water can be applied as a fine mist in the case of relatively impervious products such as peppercorns or by steaming in more difficult applications.

If surface wetting is a technical requirement, then mild surface drying post-treatment will promote the volatilization of surface acids thereby reducing acidulation. Alternatively, post-treatment surface addition of approximately 0.2% w/w of sodium bicarbonate will, in most cases, neutralize all surface acidulation.

Once the desired exposure is attained, the vacuum in the vessel may be released and the treated products proceed to final packaging stages. The method of the present invention is further advantageous in that it provides some protection against post-treatment thus permitting mechanical and/or human double handling.

It is preferable, however, that once the surface acidulation has been decreased to minimize unfavorable acidic flavors, sometimes a requirement with bland materials, the material is handled and packed in such a manner as to minimize any further microbial contamination especially if a favorable environment exists to initiate and support further microbial growth.

Turning to the drawings, in FIG. 1, material 2 to be treated is provided in a sanitary pressure vessel 1. The vessel 1 comprises a hinged swing away lid 3 which contains a flange and seal 4. The vessel 1 is also provided with a safety vent 8, a pressure/vacuum gauge 9, a pressure regulator valve 10 and gas sparging ports 11. An external vacuum source is operably connected to vessel 1 by means of a line 6 and valve 7. Connected to the gas sparging ports by means of lines 12, 13, 14, 15 and valves 16, 17 and 18 is a compressed gas source 19, one or more volatile substance sources 20, preferably sparging vessels, and an aerosol trap 21.

The aerosol trap 21 is intended to minimize the formation of large droplets of the volatile(s) during sealing of the vessel 1. These large aerosol droplets cause undesirable spotting of the material to be treated and non-uniform distribution of the volatile(s) or the material surface. Multiple volatile substance sources 20 ensure complete saturation of the carrier gas.

Where the volatile substance is carbonic acid, the volatile source 20 may be at least initially filled with purified water such that bubbling of the $CO_2$ gas therethrough produces carbonic acid thus causing the $CO_2$ carrier gas to be at least partially saturated with the produced carbonic acid. Some materials will benefit more after the carrier gas, preferably food grade carbon dioxide, has been passed through multiple volatile substance sources to achieve a mixture of volatiles in the carrier gas. Various types, combinations and concentrations of volatile substances can be used to treat the substrate material to optimize shelf life and flavor parameters, particularly various mixtures of acetic and carbonic acids and hydrogen peroxide. A carrier gas/multiple volatile mixture may be provided by mixing a group of parallel gas/volatile mixture streams after passing through their respective volatile substance sources or, a single carrier gas stream may be passed through a series of volatile substance sources.

In use, a batch of material 2 to be treated is introduced through the lid 3 into the vessel 1 and the lid is then sealed. Valve 7 is opened and evacuation is commenced by means of the vacuum pump 5. When the desired vacuum is achieved valves 16, 17 and 18 are opened and the carrier gas is forwarded from the compressed gas source 19 to the volatile substance source 20, the volatile substance thereby becoming entrained in the carrier gas, which is then introduced into the vessel 1 through sparging ports 11 to contact the material 2. Valves 22 and 23 may be operated to bypass the additional volatile substance source 20 if only one volatile substance is required.

During the process the carrier gas, which is at least partially stripped of the volatile substance, is allowed to escape through the pressure regulator valve 10 achieving a desired process overpressure for the predetermined time of exposure. The stripped carrier gas may be recycled back to the process as mentioned above for further entrainment of the volatile substance.

The duration of exposure is optimized to provide the maximum reduction in microbial bioburden while achieving the desired flavor and or the properties of the material 2 being treated. Once the desired exposure is attained, the flow of carrier gas is ceased and the pressure regulating valve 10 released. The treated material 2 is then removed from the vessel and sealed in a suitable packaging material.

As mentioned above, the inventive method is suitable for use with any volatile substance which may chemically and/or physically alter the treated material to reduce microbial contamination thereby extending the shelf life thereof. The method is particularly suitable for use with natural food acids such as acetic acid and carbonic acid. Acetic acid is a natural organic food acid with a high degree of biocidal activity and is highly soluble in carbon dioxide. The pH profile of acetic acid is shown in Table 1.

TABLE 1 pH PROFILE ACETIC ACID

| % Acetic Acid- Aqueous Solution | pH |
| --- | --- |
| 90 | −0.01 |
| 60 | 1.17 |
| 45 | 1.52 |
| 15 | 1.73 |
| 11 | 1.83 |

Surprisingly, it has been found in accordance with the present invention that carbonic acid is also useful as a volatile treatment substance. Carbonic acid is also a natural organic food acid, which has been found to possess a high degree of biocidal activity. It is also soluble in gaseous carbon dioxide and has a high degree of buffering capacity. Unexpectedly the applicants have determined that carbonic and acetic acids utilized in accordance with the method yield similar titrateable acidities after the gas mixes are "stripped" of their acids by passing them through distilled and neutralized water as shown in Table 2 below.

As a quality assurance method and to determine the titrateable acidity of acetic acid in a carrier gas as compared to carbonic acid in a carrier gas, the respective gaseous mixtures were passed through a neutralized distilled water bath and titrated with 0.1 N KOH solution until a bromothymol blue indicator yielded the first faint blue color which persisted for at least five seconds. It can be seen from Table 2 that the titrateable acidity of acetic acid and carbonic acid is virtually identical. Furthermore, an investigation by CSIRO Australia (Report FSQ96-128) concluded that the titrateable acidities were identical.

TABLE 2

ACID IN $CO_2$ CARRIER

| MIXTURE | VOL. DIS. $H_2O$ | REACTION TIME (SECONDS) | FLOW RATE $CO_2$ | TITER 0.1 N KOH |
| --- | --- | --- | --- | --- |
| Acetic Acid | 200 | 10 | 10 l/minute | 44 mils |
| Acetic Acid | 200 | 10 | 10 l/minute | 38 mils |
| Acetic Acid | 200 | 10 | 10 l/minute | 41 mils |
| Carbonic Acid | 200 | 10 | 10 l/minute | 43 mils |
| Carbonic Acid | 200 | 10 | 10 l/minute | 38 mils |

Figure 2:
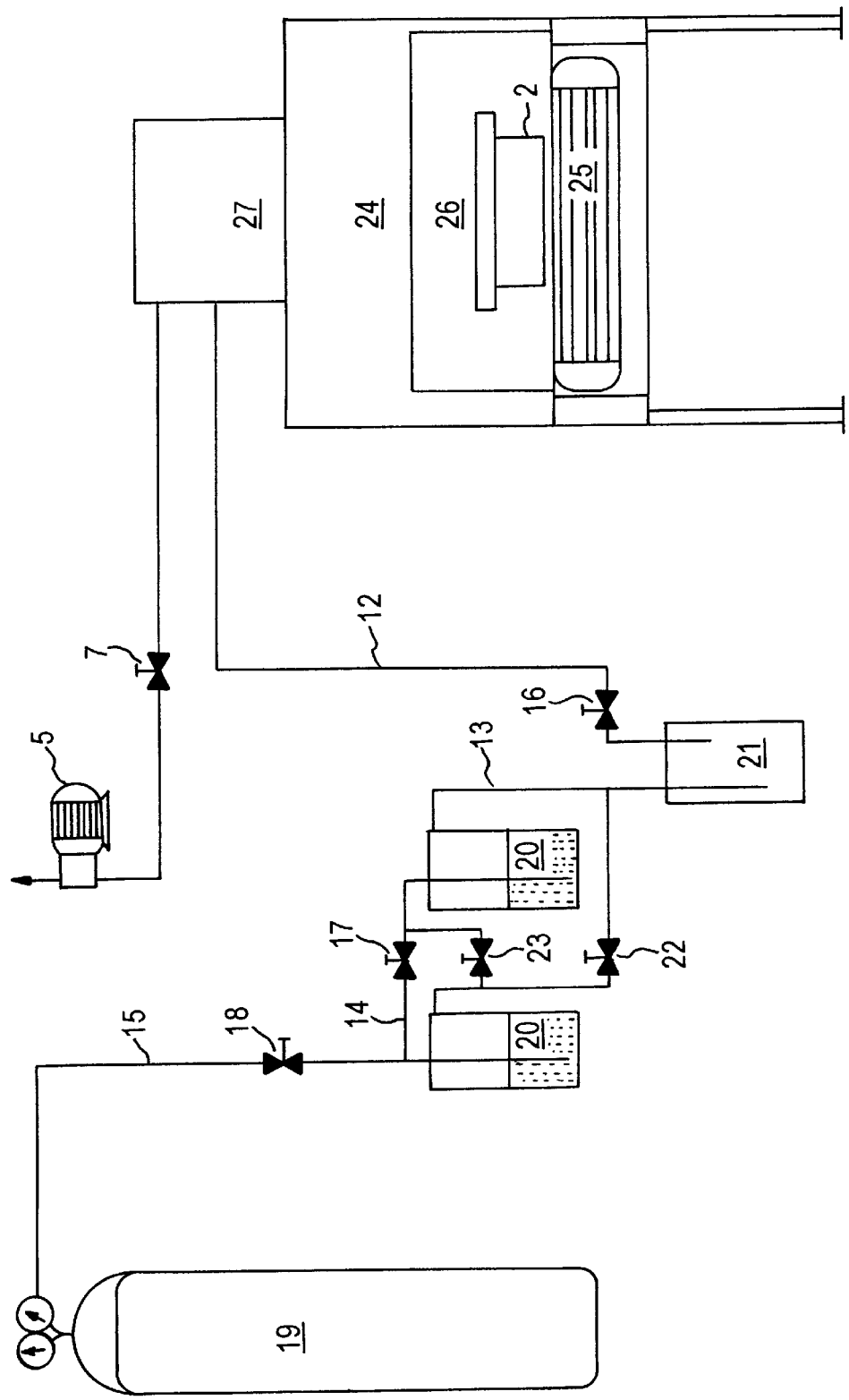
FIG. 2 is a schematic elevational representation of a continuous treatment apparatus according to a second embodiment of the present invention.

As shown in FIG. 2, an alternative application to the batch process is to conduct the method of the invention continuously while conveying material through a commercially available flow wrapper 24, or similar packaging system, equipped with a conveyor 25, a gas sparging head 26 and a gas control system 27.

Typically, the method can be balanced to attain treatment times of only seconds. Of course longer treatment times may be necessary depending upon a number of variables including initial microbial content. The short processing time can yield up to 30 days and longer extension in the acceptable shelf life of bread and other baked products. Shelf life is evaluated on the basis of flavor and aroma profiles, as well as and visible evidence of fungal and/or bacterial spoilage.

Figure 3:
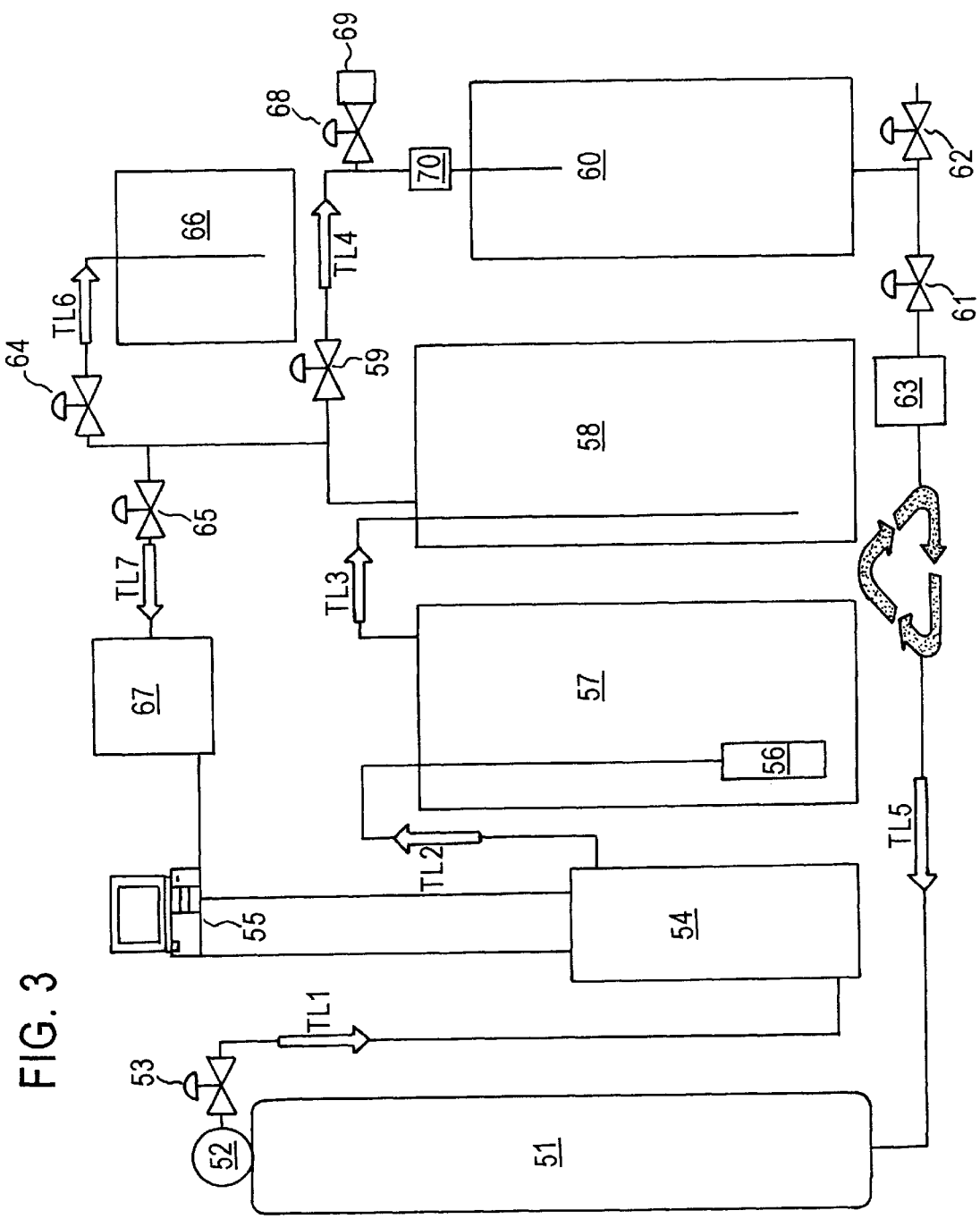
FIG. 3 is a flowchart of the treatment method and apparatus according to a third embodiment of the present invention.

An alternative embodiment of an apparatus for carrying out the inventive method is shown in FIG. 3 in which compressed gas, typically carbon dioxide, from a source 51 passes through regulator 52 when valve 53 is opened. The carrier gas is transferred through transfer line TL1, to flow meter 54. Process controller 55 monitors and controls the flow of carrier gas through the flow meter 54 at a predetermined rate. The carrier gas is then transferred through line TL2 to the sparger 56, and sparged through the volatile substance contained in vessel 57. As mentioned above, the inventive method can include one or more such vessels to provide a mixture of volatile substances in the carrier gas. If carbonic acid treatment is required vessel 57 may be at least initially filled with water.

Preferably the carrier gas is saturated with volatile substance(s). The carrier gas/volatile substance mixture is then transferred through line TL3 into the liquid trap 58, to ensure that an aerosol is not transferred into line TL4. In operative mode, the gas mixture is then normally transferred through line TL4 and through valve 59, with valves 64 and 68 closed, through heating manifold 70, which is normally not in heating mode, through to product treatment container 60, which may be the final packaging; vacuum/pressure vessel; treatment tunnel or other such device as indicated in FIGS. 1 and 2.

After the prescribed treatment, the carrier gas stripped of volatile(s) may be transferred through line TL5 with valve 61 open and valve 62 closed, to compressor 63, and recycled back to compressed gas cylinder 51. Alternatively after leaving treatment container 60 the volatile(s) stripped carrier gas can be vented to the atmosphere with valve 61 closed and valve 62 open.

When a material is not being treated but it is desirable to maintain the carrier gas/volatile substance flow, especially in the case of treatment with carbonic acid, valve 59 is closed and valve 64 is opened with valve 65 closed, the carrier gas/volatile substance mixture is transferred through line TL6 to water scrubber 66 where the volatile substance is stripped from the carrier gas and the gas is vented to atmosphere or recycled.

Quality measurements of the carrier gas and the volatile substance are performed by closing valves 59 and 64 and opening valve 65, transferring the gas mixture through line TL7 to quality control station 67 for testing. Test data from control station 67 is sent to process controller 55 which monitors and controls the flow of carrier gas through the flow meter 54. If station 67 identifies that the carrier gas is being slowly diluted by atmospheric gas the process controller 55 may increase the flow rate through flow meter 54, until the predetermined maximum volatile substance transfer rate is achieved, at which point a predetermined percentage of recycled carrier gas is vented to the atmosphere and an equivalent volume of new carrier gas fed into the circuit from compressed carrier gas vessel 51.

If a high concentration of a volatile substance or a mixture of volatile substances is required for a given application, the standard carrier gas/volatile substance mixture transferring through line TL4 may be dosed with additional volatiles by injection of a fine aerosol of the desired volatile substance from a storage tank/atomizer 69 through opened valve 68. The gas mixture/aerosol continues to transfer along line TL4 and is heated to beyond the vaporization point of the added aerosol in the heated manifold 70, from where it enters the treatment container 60 as normal. Prolonged production runs employing this additional dosage system may cause condensation on the inner walls of treatment vessels/tunnels if they are not heat lagged.

The following examples illustrate and substantiate various aspects of the present invention, but are not intended in any way to be limiting thereon.

EXAMPLE 1A

Sandwich Ham

Samples of sandwich ham were placed in a suitable vessel capable of evacuation which was then evacuated. The samples were treated a $CO_2$/acetic acid gas mixture or $CO_2$/carbonic acid gas mixture, respectively, for designated periods. The gas flow was constant such that the vessel maintained an overpressure 0.01–2 bar above atmospheric pressure. The sandwich ham samples were in plastic bags and a degree of pressure was allowed to develop in the plastic bags during treatment. After the designated period the gas flow was stopped, the bags containing the ham were closed and shaken slightly for 15 seconds to provide better contact with the carrier gas/volatile substance mixture. The vessel was then vacuum flushed again and an additional exposure to the respective gas mixtures performed along with the 15 second post-treatment contact.

The majority of the gas mixture entering the vessel escaped with approximately 50% of the residual gas mixture being expelled manually prior to sealing of the plastic bags. The samples were then stored for approximately one hour prior to microbiological analysis. The results are provided in Table 3.

As can be seen from Table 3, there has been a substantial reduction in the bioburden following application of the method of the invention. For treatment with the carrier gas/acetic acid mixture, the initial total plate count of $3.4 \times 10^4$, and total spores of 35 was reduced to total plate count 65 and 70, total spore count 10 and 40, respectively. Using a carrier gas/carbonic acid mixture, an initial total plate count of $2 \times 10^6$ and total spores of 250 was reduced to total plate count of $7 \times 10^3$ and total spores 500 at gas flow rate of 10 liters/minute. At a higher gas flow rate of 20 liters/minute total plate count was reduced to less than 10 and total spores to 45.

EXAMPLE 1B

Sandwich Ham

In this example, samples of sandwich ham were treated according to the procedure of Example 1A with a volatile substance comprising 50% carbonic acid and 50% hydrogen peroxide.

Shelf life observations were made approximately four days after treatment and further observations were made from nine to twenty days after treatment. The results are provided in Table 4.

It can be seen from the microbiological results provided under Table 4 that this particular gas mixture is very effective in reducing the microbiological count. Total treatment times of 10, 20 and 60 seconds resulted in proportional reductions down to 2 vegetative and less than 1 spore organism per gram of sample.

It has been observed that hydrogen peroxide increases the pink coloration and extends the shelf life of the pink coloration of some smallgoods. This effect appears to be intermediatory in efficiency between carbonic and acetic acids. Again, smoked aromas were observed along with slight background volatility in some instances.

EXAMPLE 2A

Crumpets

Crumpet fingers were treated according to the procedure of Example 1A with carbonic acid and a weight mixture of 90% acetic acid, 10% carbonic acid. The results for carbonic acid are provided in Table 5A and those for the acetic acid/carbonic acid mixture in Table 5B.

As can be seen from Table 5A, a significant seven day shelf life extension of crumpets was achieved with $CO_2$/carbonic acid gas mixture treatment. Not all mold spores were killed or completely inhibited, however, colony growth was random indicating entire surface area had been uniformly treated. No unfavorable acidic flavors were detected. A six second exposure time was found to be optimal. Greater exposures appeared to make no improvement. Indeed it is not entirely clear why higher exposure times did not result in additional benefit. This appears to be a peculiarity of treatment with carbonic acid.

For treatment with $CO_2$/acetic acid-carbonic acid mixture an indefinite shelf life extension was achieved however, after assessing the resultant surface acidulation the realistic shelf life extension was reduced to 13 days. The manufacturers of these types of products must consider other quality parameters such as syneresis and related textural problems which may further reduce the shelf life extension, however the inventive method will still achieve a significant increase in food safety to the consumer.

EXAMPLE 2B

Crumpets

Crumpet fingers were treated in accordance with the procedure of Example 1B. The results are given in Table 6. It can be seen from the microbiological results provided under Table 6 that the mixture of carbonic acid and hydrogen peroxide is very effective in reducing the microbiological counts. Total treatment times of 10, 20 and 60 seconds resulted in proportional reductions down to six vegetative and less than 1 spore organism per gram of sample.

EXAMPLE 3A

Peppercorns

Utilizing the procedure of Example 1A, a $CO_2$/acetic acid mixture was applied to the surface of wetted black peppercorns.

EXAMPLE 3B

Peppercorns

Black peppercorns were subjected to four separate treatments of 300 seconds each at 0 hours; 12 hours; 13 hours and 16 hours. Prior to all treatments except the 16 hour treatment, the peppercorns were wetted with 2.0% w/w of water to ensure continuity of acid transfer.

Due to the peppercorns low water activity of 0.75, wetting with water is required. This was achieved by pouring a specified quantity of distilled water onto the peppercorns while continuously mixing in a plastic bag. A new plastic bag was then used for the gaseous treatment of the subject invention. For effective wetting, it is essential to completely wet the entire surface while minimizing the amount of added water. This example was intended to assess the effect of increasing the time of contact between the gaseous mixture and the peppercorns at high surface acidity concentrations.

EXAMPLE 3C

Peppercorns

Black peppercorns were subjected to treatments of 900 seconds each at 0 seconds; 900 seconds; 1 800 seconds and 2700 seconds. All treatments except the first treatment were preceded by wetting with 1.0% w/w of water to ensure continuity of acid transfer. The intent of this example was to assess the effect of increasing the contact time to three weeks at high surface acidity concentrations. The results for examples 3A–3C are shown in Table 7.

Peppercorns have traditionally been a difficult material to sterilize and this is evidenced in the high bioburden of the controls and results even with long exposure times. However a significant reduction in sporer organisms from $2.7 \times 10^7$ to less than $10 \times 10^4$ was achieved with example 3B at 20 hours.

Longer exposure times and contact times of example 3C only marginally improved the overall efficiency of the inventive method. However a significant reduction in spores from $2.7 \times 10^7$ to $5.2 \times 10^4$ was achieved.

EXAMPLE 3D

Peppercorns

Black peppercorns at 0.75 $A_w$ were treated in accordance with the procedure of Example 1B without the addition of any surface water. The results are shown in Table 8.

It can be seen from the microbiological results provided under Table 8 that the mixture of carbonic acid and hydrogen peroxide was the most effective in reducing the microbiological counts in black peppercorns. Total treatment times of 10; 20 and 60 seconds resulted in close to proportional reductions down to $9.0 \times 10^7$ vegetative and $7.5 \times 10^3$ spore organisms per gram of sample.

Although the nature of hydrogen peroxide did not require a high water activity for "transference" to the peppercorn, it is not entirely clear whether all of the carbonic acid in the carrier gas would have been deposited on the peppercorn surface. It is believed that the actual proportions of the individual volatile substances, in the volatile substance sources, or entrained in the carrier gas may differ from the proportions that actually make contact with the material being treated. The mechanism of transfer is not yet entirely understood. Not wishing to be bound by any particular theory, the applicants assume that there are at least significant quantities of each individual volatile substance present in the carrier gas which transfer to the material being treated. However, it is thought that the hydrogen peroxide at least would react more evenly if the peppercorns were at a higher water activity. The volatile/oxidant flavor which was just perceptible at the 60 second exposure time would not normally be noticeable in this materials end application. From the data collected to date, it is clear that exposure time and volatile concentration typically increase the efficiency of this inventive method. It is also expected that an increase in pressure and temperature may assist the efficiency of the inventive method.

Some heat treatment experiments performed at maximum acetic acid concentrations of 0.08%, which is negligible, indicate that the spore organisms are highly stressed. It is also expected that the inventive method may utilize surface heat of the material to volatilize any excessive acidic volatiles i.e. reduce acidulation.

It has also been found that even with low acetic acid concentrations, if the treatment vessel is maintained at an over-pressure of up to 3 bar over atmospheric pressure, up to five days shelf life extension may be obtained on crumpets.

It can be seen that the present inventive method is not only suitable as a biocidal method but in lower concentrations has an inhibitory function and substantially extends the shelf life of certain products.

It is also envisaged that, where the volatile substance is other than acetic acid, the inclusion of a low concentration of acetic acid in the mixture may increase the post-protection potential thereof. Typically, a preferred volatile substance mixture would contain, by weight, about 10–20% acetic acid, about 30–40% hydrogen peroxide, with the balance carbonic acid.

It has been found that some food products, treated by the method of the invention, particularly bland food products can develop a slightly acidic taste. This can be masked by the use of spreads or condiments or flavor masking agents. By means of the invention it is possible to treat a material with a volatile substance to alter its physical or chemical characteristics while not severely adversely affecting the properties of the treated material. The method of the invention does not require specialized packaging or costly changes to existing equipment.

It will be appreciated by persons skilled in the art that numerous variations and/or modifications may be made to the invention without departing from the scope of the invention as described.

TABLE 3

ACETIC/CARBONIC ACID - SMALLGOODS

| FOODSTUFF | VOLATILE | QA (QUALITY ASSURANCE) | FLOW RATE OF GAS MIXTURE | EXPOSURE TIME (SECONDS) | MICRO ANALYSIS (per gram) | SURFACE AREA/ SAMPLE WEIGHT |
|---|---|---|---|---|---|---|
| Sandwich ham control ($A_w$ = 0.95) | | | | | TPC = $3.4 \times 10^4$   TSP = 35 | 40.5 cm$^2$/10 g |
| Sandwich ham | Acetic Acid | | 22 l/minute | 16 | TPC = 70   TSP = 10 | 10 g |
| Sandwich ham | Acetic Acid | 38 ml | 22 l/minute | 20 | TPC = 65   TSP = 40 | 20 g |
| Sandwich ham control ($A_w$ = 0.95) | | | | | TPC = $2 \times 10^6$   TSP = 250 | 40.5 cm$^2$/10 g |
| Sandwich ham | Carbonic Acid | 43 ml | 10 l/minute | 50 | TPC = $7 \times 10^3$   TSP = 500 | 10 g |
| Sandwich ham | Carbonic Acid | | 20 l/minute | 50 | TPC < 10   TSP = 45 | 10 g |

$A_w$ - Surface water activity
TPC - total plate count/gram
TSP - total spores/gram

TABLE 4

50% CARBONIC ACID/50% HYDROGEN PEROXIDE - SMALLGOODS

| FOODSTUFF | VOLATILE | FLOW RATE OF GAS MIXTURE | EXPOSURE TIME | SHELF LIFE OBSERVATIONS MICRO ANALYSIS/g | SAMPLE WEIGHT |
|---|---|---|---|---|---|
| Sandwich ham (control) | 50% carbonic acid/50% hydrogen peroxide | 22 liters/minute | 0 | DATA REQUIRED TPC = $2.6 \times 10^6$   TSP = $1.35 \times 10^6$ | 10 g |
| Sandwich ham | 50% carbonic acid/50% hydrogen peroxide | 22 liters/minute | 10 seconds | 4 days - pinker than control sample at 0 hours: slight volatile aroma with smoke background
9 days - slightly greyer: no observable microbial activity or degradation
13 days - 50% surface grey; no observable microbial activity or degradation
TPC = $2.1 \times 10^4$   TSP = $2.6 \times 10^4$ | 10 g |
| Sandwich ham | 50% carbonic acid/50% hydrogen peroxide | 22 liters/minute | 20 seconds | 4 days - 30% surface area pinker than control at 0 hours. Remainder grey. Smoke aroma strong and dominant
9 days - slightly greyer: no observable microbial activity or degradation
18 days - 50% surface grey; no observable microbial activity or degradation.
TPC = $6.3 \times 10^2$   TSP = $\times 10^2$ | 10 g |
| Sandwich ham | 50% carbonic acid/50% hydrogen peroxide | 22 liters/minute | 60 seconds | 4 days - pinker than 10 second sample. Slight volatile aroma with smoke background.
9 days - slightly greyer: no observable microbial activity or degradation.
20 days - 80% surface pinker than control sample at 0 hours
TPC = 2   TSP < 1 | 10 g |

TABLE 5A

CARBONIC ACID - BAKED GOODS

| FOODSTUFF | VOLATILE | QA (QUALITY ASSURANCE) | FLOW RATE OF GAS MIXTURE | EXPOSURE TIME (SECONDS) | SHELF LIFE OBSERVATION | SURFACE AREA/SAMPLE WEIGHT |
|---|---|---|---|---|---|---|
| Crumpets (Control) | | | | 0 | 4 days - 4 colonies | Whole Fingers |
| Crumpets | Carbonic | 38 ml | 22 l/min | 6 | 11 days 3 to 10 colonies on all samples. End shelf life due to mold growth | Whole Fingers |
| Crumpets | Carbonic | | | 10 | End shelf life due to mold growth | Whole Fingers |
| Crumpets | Carbonic | | | 16 | End shelf life due to mold growth | Whole Fingers |
| Crumpets | Carbonic | | | 20 | End shelf life due to mold growth | Whole Fingers |

TABLE 5A-continued

CARBONIC ACID - BAKED GOODS

| FOODSTUFF | VOLATILE | QA (QUALITY ASSURANCE) | FLOW RATE OF GAS MIXTURE | EXPOSURE TIME (SECONDS) | SHELF LIFE OBSERVATION | SURFACE AREA/SAMPLE WEIGHT |
|---|---|---|---|---|---|---|
| Crumpets | Carbonic | | | 26 | End shelf life due to mold growth | Whole Fingers |
| Crumpets | Carbonic | | | 32 | End shelf life due to mold growth | Whole Fingers |
| Crumpets | Carbonic | | | 40 | End shelf life due to mold growth | Whole Fingers |
| Crumpets | Carbonic | | | 50 | End shelf life due to mold growth | Whole Fingers |
| Crumpets | Carbonic | | | 60 | End shelf life due to mold growth | Whole Fingers |

TABLE 5B

ACETIC ACID - BAKED GOODS

| FOODSTUFF | VOLATILE | QA (QUALITY ASSURANCE) | FLOW RATE OF GAS MIXTURE | EXPOSURE TIME (SECONDS) | SHELF LIFE OBSERVATION | SURFACE AREA/SAMPLE WEIGHT |
|---|---|---|---|---|---|---|
| Crumpets (Control) | | | | 0 | 4 days - 5 colonies | Whole Fingers |
| Crumpets | 90% Acetic 10% Carbonic | 44.5 ml | 22 l/min | 6 | 11 days - 1 small colony weak acrid/flour aroma, no taste - raw. No aroma or taste during or after cooking | Whole Fingers |
| Crumpets | 90% Acetic 10% Carbonic | | | 0 | 15 days - 1 small dense colony. Slight acrid aroma, no taste - raw. Very slight acrid aroma, no taste - cooked | Whole Fingers |
| Crumpets | 90% Acetic 10% Carbonic | | | 16 | 15 days - no colonies. Slight acrid aroma and flavor - raw. Very slight toasted/acrid aroma and flavor - cooked. End shelf life due to deleterious flavor | Whole Fingers |
| Crumpets | 90% Acetic 10% Carbonic | | | 20 | End shelf life due to deleterious flavor | Whole Fingers |
| Crumpets | 90% Acetic 10% Carbonic | | | 26 | End shelf life due to deleterious flavor | Whole Fingers |
| Crumpets | 90% Acetic 10% Carbonic | | | 32 | End shelf life due to deleterious flavor | Whole Fingers |
| Crumpets | 90% Acetic 10% Carbonic | | | 40 | End shelf life due to deleterious flavor | Whole Fingers |
| Crumpets | 90% Acetic 10% Carbonic | | | 50 | End shelf life due to deleterious flavor | Whole Fingers |
| Crumpets | 90% Acetic 10% Carbonic | | | 60 | End shelf life due to deleterious flavor | Whole Fingers |

TABLE 6

50% CARBONIC ACID/50% HYDROGEN PEROXIDE - BAKED GOODS

| FOODSTUFF | VOLATILE | FLOW RATE OF GAS MIXTURE | EXPOSURE TIME | SHELF LIFE OBSERVATIONS MICRO ANALYSIS/g | SAMPLE WEIGHT |
|---|---|---|---|---|---|
| Crumpets (Control) | 50% carbonic acid/50% hydrogen peroxide | 22 liters/minute | 0 seconds | 1 day - 3 mold colonies, end shelf life TPC = $4.5 \times 10^4$    TSP = $2.8 \times 10^4$ | 10 g |
| Crumpets | 50% carbonic acid/50% hydrogen peroxide | 22 liters/minute | 10 seconds | 9 days - no observable microbial activity 20 days - no observable microbial activity End realistic shelf life due to leathery texture TPC = $3.6 \times 10^2$    TSP = $2.8 \times 10^2$ | 10 g |
| Crumpets | 50% carbonic acid/50% hydrogen peroxide | 22 liters/minute | 20 seconds | 4 days - one dead/stressed mold colony 9 days - no observable microbial activity 20 days - no observable microbial activity. End realistic shelf life due to leathery texture TPC = 30    TSP = < 1 | 10 g |
| Crumpets | 50% carbonic acid/50% hydrogen peroxide | 22 liters/minute | 60 seconds | 4 days - very slight oxidant note 9 days - no observable microbial activity | 10 g |

TABLE 6-continued

50% CARBONIC ACID/50% HYDROGEN PEROXIDE - BAKED GOODS

| FOODSTUFF | VOLATILE | FLOW RATE OF GAS MIXTURE | EXPOSURE TIME | SHELF LIFE OBSERVATIONS MICRO ANALYSIS/g | SAMPLE WEIGHT |
|---|---|---|---|---|---|
| | | | | 20 days - no observable microbial activity. End reatistic shelf life due to leathery texture. Shelf life extension 19 days TPC = 6  TSP = < 1 | |

TABLE 7

ACETIC ACID - PEPPERCORNS

| EXAMPLE | FOODSTUFF | VOLATILE | QA (QUALITY ASSURANCE) | FLOW RATE OF GAS MIXTURE | EXPOSURE TIME (SECONDS) | MICRO ANALYSIS/g | SURFACE AREA/SAMPLE WEIGHT |
|---|---|---|---|---|---|---|---|
| Control | Peppercorns | | | | 0 | TPC = $3.7 \times 10^7$ TSP = $2.7 \times 10^7$ | 39 g |
| 3A | Peppercorns | Acetic Acid | 38 | 12 l/min | 300 | TPC = $> 10 \times 10^6$ TSP = $5.0 \times 10^6$ | 39 g 1 g $H_2O$ (2.5%) |
| | Peppercorns | Acetic Acid | 38 | 12 l/min | 180 | TPC = $8 \times 10^6$ TSP = $1.2 \times 10^7$ | 39 g 1 g $H_2O$ (2.5%) |
| 3B | Peppercorns | Acetic Acid | 38 | 22 l/min | Exposures of 300 seconds each at 0, 12, 13 and 16 hours (total 1200) | 20 hours after first treatment TPC = $9.0 \times 10^6$ TSP = $< 10.0 \times 10^4$ | 50 g + 1 g $H_2O$ (2.0%) |
| 3C | Peppercorns | Acetic Acid | 38 | 14 l/min | 4 exposures of 900 seconds each at 0, 900, 1800, and 2700 | 3 weeks after first treatment TPC = $7.9 \times 10^4$ TSP = $5.2 \times 10^4$ | 98 g + 2 g $H_2O$ (2.0%) |

TABLE 8

50% CARBONIC ACID/50% HYDROGEN PEROXIDE - PEPPERCORNS

| FOODSTUFF | VOLATILE | EXPOSURE TIME | SHELF LIFE OBSERVATIONS MICRO ANALYSIS/g | SAMPLE WEIGHT |
|---|---|---|---|---|
| Peppercorns (control) | | 0 | TPC = $8.9 \times 10^7$ TSP = $7.1 \times 10^7$ | 10 g |
| Peppercorns | 50% carbonic acid 50% hydrogen peroxide | 10 | TPC = $6.9 \times 10^5$ TSP = $5.6 \times 10^5$ | 10 g |
| Peppercorns | 50% carbonic acid 50% hydrogen peroxide | 20 | TPC = $6.9 \times 10^4$ TSP = $4.1 \times 10^3$ | 10 g |
| Peppercorns | 50% carbonic acid 50% hydrogen peroxide | 60 | 4 days - threshold volatility detected by taste and aroma TPC = $9.0 \times 10^3$ TSP = $7.5 \times 10^3$ | 10 g |

We claim:

1. A method for reducing the viable microbial content of a solid material for human consumption which is susceptible to microbial spoilage, said method comprising:

(a) placing the material in a vessel capable of evacuation;

(b) evacuating the vessel; and (c) contacting exposed surfaces of the material with a gas mixture comprising a major portion of a carrier gas and a minor portion of a volatile substance selected from the group consisting of natural food acids, chemical biocides and mixtures thereof for a contacting period of 60 seconds or less during which period the volatile substance partitions into solution upon said exposed surface, wherein at the time of contacting the exposed surfaces of the material with said gas mixture, the exposed surfaces of the material have a water activity ($A_w$) of greater than or equal to 0.85.

2. A method according to claim 1, wherein (b) and (c) are repeated sequentially.

3. A method according to claim 1, wherein (c) comprises feeding the gas mixture to the vessel to achieve a desired over-pressure in the vessel during the contacting period.

4. A method according to claim 1, wherein (c) comprises continually feeding the gas mixture to the vessel to maintain a desired over-pressure in the vessel during the contacting period.

5. A method according to claim 4, wherein the over-pressure is up to 3 bar (2250 mm Hg) above atmospheric pressure.

6. A method according to claim 2, wherein prior to repeating (b) and (c), said material is agitated.

7. A method according to claim 1, wherein (c) comprises contacting the exposed surfaces of the material with a gas mixture comprising a major portion of a carrier gas and a minor portion of a volatile substance selected from the group consisting of natural food acids, chemical biocides and mixture thereof for a contacting period of 30 seconds or less.

8. A method according to claim 1, wherein (c) comprises contacting the exposed surfaces of the material with a gas mixture comprising a major portion of a carrier gas and a minor portion of a volatile substance selected from the group consisting of natural food acids, chemical biocides and mixture thereof for a contacting period of 10 seconds or less.

9. A method according to claim 1, wherein the material to be treated is chosen from the group consisting of foods, pharmaceutical compositions, and ingredients of pharmaceutical compositions.

10. A method according to claim 9, wherein the volatile substance is a natural food acid.

11. A method according to claim 10, wherein the natural food acid is acetic acid.

12. A method according to claim 10, wherein the natural food acid is carbonic acid.

13. A method according to claim 9, wherein the volatile substance is a chemical biocide.

14. A method according to claim 13, wherein the chemical biocide is hydrogen peroxide.

15. A method according to claim 9, wherein the volatile substance present in the gas mixture is a mixture of acetic acid and carbonic acid.

16. A method according to claim 15, wherein the volatile substance present in the gas mixture consists of 90% (w/w) acetic acid and 10% (w/w) carbonic acid.

17. A method according to claim 9, wherein the volatile substance present in the gas mixture is a mixture of carbonic acid and hydrogen peroxide.

18. A method according claim 17, wherein the volatile substance present in the gas mixture consists of 50% (w/w) carbonic acid and 50% (w/w) hydrogen peroxide.

19. A method according to claim 9, wherein the volatile substance present in the gas mixture is a mixture of acetic acid, carbonic acid and hydrogen peroxide.

20. A method according to claim 19, wherein the volatile substance present in the gas mixture consists of 10–20% (w/w) acetic acid, 50% (w/w) carbonic acid and 30–40% (w/w) hydrogen peroxide.

21. A method according to claim 1, wherein the carrier gas is saturated with the volatile substance.

22. A method according to claim 1, wherein the volatile substance is entrained in the carrier gas by passing the carrier gas through a vessel(s) containing the volatile substance(s) in liquid form.

23. A method according to claim 1, wherein the volatile substance is prepackaged with the carrier gas.

24. A method according to claim 1, wherein the volatile substance is injected directly into a gas line feeding the carrier gas to the vessel thereby forming said gas mixture.

25. A method according to claim 24, wherein after said volatile substance is injected, said gas line is heated to maintain said gas mixture in the gaseous state prior to entry into said vessel.

26. A method according to claim 1, wherein the vessel is initially evacuated rapidly to sub-ambient pressure.

27. A method according to claim 1, wherein the carrier gas is carbon dioxide and/or nitrogen gas.

28. A method according to claim 1, wherein the method is conducted either batchwise or continuously.

29. A method according to claim 1, wherein at the time of contacting exposed surfaces of the material with said gas mixture, the water activity ($A_w$) of exposed surfaces of the material is greater than or equal to 0.95.

30. A method according to claim 1, further comprising:
(d) packing the material within gas barrier packaging to form and/or maintain an atmosphere of said volatile substance substantially in equilibrium with the volatile substance that has partitioned into the solid material.

* * * * *